United States Patent [19]

Waldbillig

[11] 4,300,571
[45] Nov. 17, 1981

[54] CONSTANT FLUSH DEVICE

[75] Inventor: Charles C. Waldbillig, Columbus, Ohio

[73] Assignee: Medex Inc., Hilliard, Ohio

[21] Appl. No.: 61,305

[22] Filed: Jul. 27, 1979

[51] Int. Cl.³ .............................................. A61B 5/02
[52] U.S. Cl. ................... 128/673; 128/214 R; 128/214 E; 128/274; 251/342
[58] Field of Search ................ 128/673–675, 128/214 R, 274, 214 F, 214 E; 251/4, 7, 117, 334, 342

[56] References Cited

U.S. PATENT DOCUMENTS

| | | | |
|---|---|---|---|
| 2,706,101 | 4/1955 | Cantor | 251/342 X |
| 2,946,555 | 7/1960 | Cantor | 251/342 |
| 3,298,367 | 1/1967 | Bergman | 128/214 R |
| 3,581,733 | 6/1971 | Grandjean | 128/673 |
| 3,626,959 | 12/1971 | Santomieri | 251/342 X |
| 3,675,891 | 7/1972 | Reynolds et al. | 128/673 X |
| 4,192,303 | 3/1980 | Young et al. | 128/214 R |
| 4,210,178 | 7/1980 | Morse et al. | 128/214 R X |

OTHER PUBLICATIONS

The Deseret Company, "Delta-Flow" Catalogue No. 1280, Jun. 1978.

*Primary Examiner*—Kyle L. Howell
*Attorney, Agent, or Firm*—Wood, Herron & Evans

[57] ABSTRACT

A blood pressure monitoring system in which an intravascular catheter is connected through flexible tubing to a transducer. The tubing between the catheter and the transducer is filled with physiological solution supplied from a bag under pressure of approximately 300 mm. of mercury. The supply line from the bag to the tube is in series with a capillary so that after the system is filled with the physiological solution, the capillary passes fluid from the supply to the catheter at the rate of around two to seven cc. per hour. Provision is made for bypassing the capillary for the purpose of fast flushing the system as would occur when the system is initially filled with fluid. The fast flush line consists of a plug in series with the line from the supply, the plug having upstream and downstream longitudinal grooves separated by a central collar. A flexible tube surrounds the plug and blocks passage from the upstream and downstream groove past the collar. The tube has a pull tab overlying the position of the grooves. Fast flushing is accomplished by pulling on the tab so that the fluid in the upstream groove can flow over the collar into the downstream groove.

2 Claims, 6 Drawing Figures

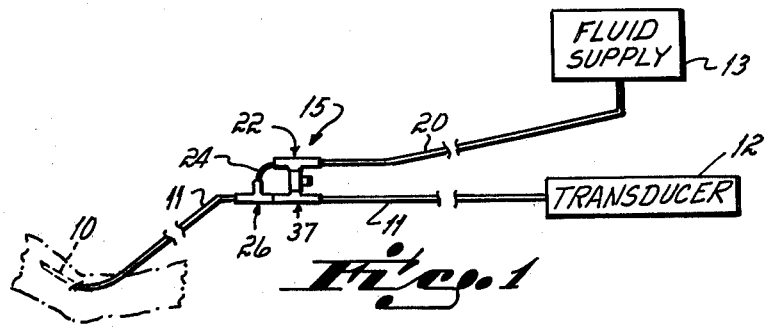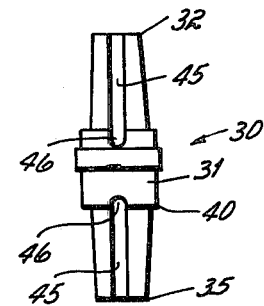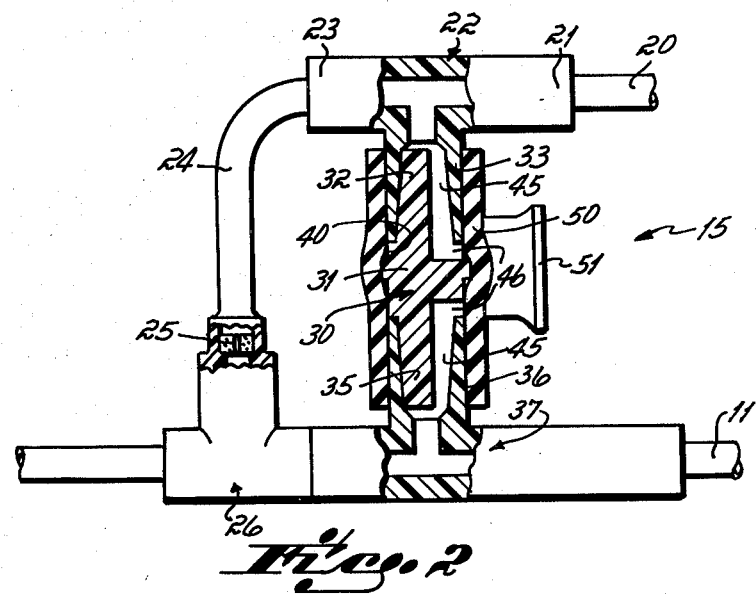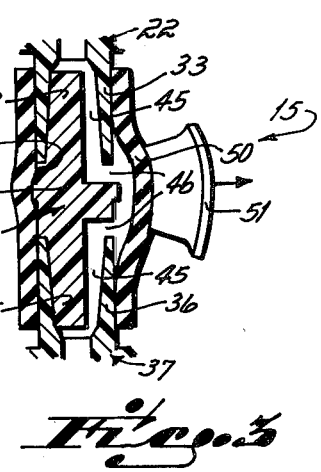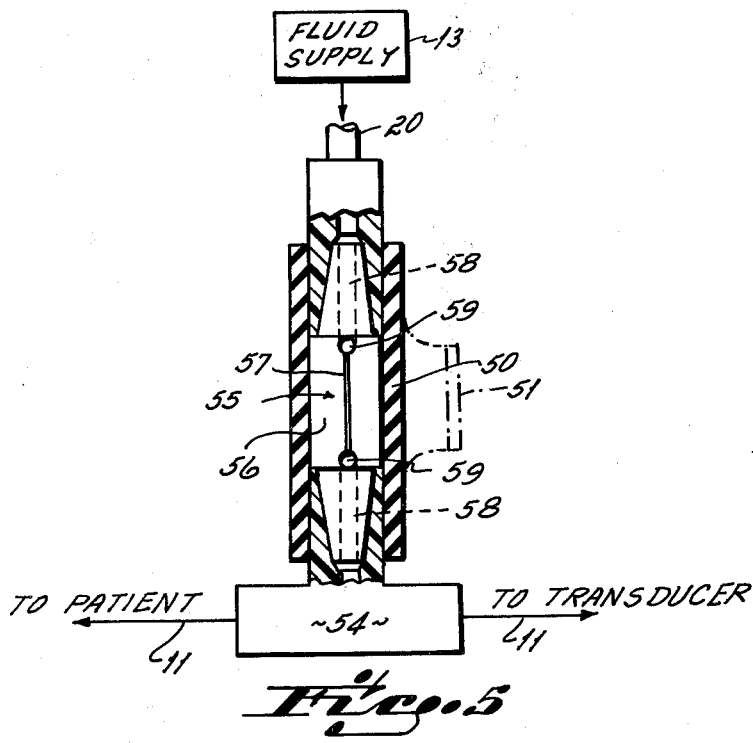

CONSTANT FLUSH DEVICE

This invention relates to a constant flush system and particularly to the fast flush valve structure for such a system. One such system to which the present invention is directed is depicted in my copending application Ser. No. 953,036.

The constant flush system is for the purpose of monitoring blood pressure of a patient by inserting a catheter into the patient's blood vessel. The catheter is connected to a tube filled with a physiological solution, the other end of the tube being connected to a transducer. Pressure from the patient's blood is transmitted via the physiological solution to the transducer and signals from the transducer are graphically recorded. The solution to the main tube is supplied through a fitting, the supply being under a pressure of approximately 300 mm. of mercury. The supply has two passages to the main tube. One is through a very small capillary orifice which permits a flow of three or six cc. per hour. The purpose of that very slight flow is to move the physiological solution continuously through the catheter to constantly flush it and thus to avoid such coagulation of blood in the catheter as would adversely affect the operation of the system.

A second, normally blocked, fast flush passageway is provided as a bypass to the capillary passageway. The fast flush passageway is used only occasionally as in filling the main tube at the time the monitoring system is installed in the patient or in flushing out blood from the main tube if blood has been withdrawn from the patient via the main tube during administration to the patient.

In addition to the system of my copending application, several constant flush systems are known. In one, a housing encloses the capillary which is mounted in series with the main tube. The housing also contains a bypass for fast flushing purposes having a resilient valve normally urged to a closed position and having a stem projecting externally of the housing by which the valve can be opened. See U.S. Pat. No. 3,675,891.

In another system, the capillary is contained in a plug having a central collar. An elastomeric sleeve surrounds the plug and is used to connect the plug in series with the supply to the main tube. Normally, the solution flows through the capillary and plug, but when it is desired to fast flush, the resilient tube around the plug may be pinched so as to deform it and create a passage around the central collar. Both of these systems have their disadvantages. For example, the first mentioned system is not reliably flushed. The valve sometimes seems to jam and the stem is susceptible to breaking off. Further, the attendant cannot conveniently vary the flow during flush from a slow flush to a rapid flush. The user must also use both hands to operate the device or must rigidly mount the device.

The latter flush device is hard to manipulate, hard to teach someone how to manipulate it and does not provide a good frequency response. As to the former point, there is nothing about the system which visually suggests how to fash flush it, that is, that squeezing of the tube is going to open up a passageway for flushing. As to the latter point, the fluid in the main tube is exposed to a substantial area of the resilient material of the sleeve where it surrounds the collar. That resilient area of the sleeve absorbs pulsations from the patient's blood vessel and thus prevents them from directly impacting on the transducer diaphragm.

An objective of the present invention has been to provide a constant flush system which is simple to construct and operate and which has a good frequency response. The invention is particularly directed to the flush valve structure wherein a resilient sleeve surrounds a plug to form the flush valve. Use of a resilient sleeve surrounding a plug as a valve is not novel per se. See the Cantor U.S. Pat. No. 2,946,555, for example. However, in accordance with the present invention, the plug is specially designed and specially mounted with respect to the other fittings in the system as to overcome the disadvantages of the prior systems and to provide advantages of its own.

More specifically, the plug has a central blocking collar and has upstream and downstream longitudinal grooves extending from said collar to the ends of the plug. A resilient sleeve surrounds the plug and blocks flow from one groove through the collar to the other groove. The sleeve has a pull tab overlying the area of the grooves and when the tab is pulled, the sleeve deforms with respect to the collar thereby permitting flushing fluid to flow around the collar into the main tube of the system.

Further, the end portions of the plug are of the reduced diameter and are snugly insertable into fittings by which the flush valve is connected between the supply tubing and the main tube. The outside diameters of the fittings are substantially the same as the outside diameter of the collar so that a smooth transition is made between the fittings and the collar and minimizes the possibility of air entrapment. The collar has small, radially-extending grooves which form continuations of the longitudinal grooves. When the resilient sleeve is in place, the only resilient area which is exposed to the fluid in the main tube is a small hole (about 0.090") formed by the radial groove in the collar and the fitting which abuts the collar. Thus, there is no measurable absorption of pulsation pressure by the resilient sleeve and thus the resilient sleeve has no deleterious effect on the frequency response of the system.

Among the advantages of the present invention, including the good frequency response referred to above, are the following:

The sleeve can be operated by pulling on the tab or by squeezing, each having its own advantages. For example, pulling on the tab permits the attendant to control rather precisely the rate of flow of the flushing fluid. Two hands are required. The squeezing method of operating the flush valve, while not as precise, permits a one-handed operation.

The system is tapped into the main tube so that the main tube is in a straight line between the transducer and the catheter in the patient.

The parts are highly visible so that if any bubbles are in the system, they can be readily seen.

The tab on the resilient sleeve provides visual and instantaneous teaching of how to operate the flush valve.

In an alternative form of the invention, the capillary is formed in the plug thereby simplifying the manufacture of the system. The capillary may be formed centrally through the plug, or more preferably, the capillary may be formed by creating a groove in the surface of the central blocking collar. That groove can be formed by a laser or by a tool. When formed, it cooperates with the sleeve to provide the capillary for a continuous flow path to the plug. If flushing is desired, the resilient sleeve is deformed as described above to permit liquid to flow past the central collar.

The several features and objectives of the present invention will become more readily apparent from the following detailed description taken in conjunction with the accompanying drawings in which:

FIG. 1 is a diagrammatic view of the overall system;

FIG. 2 is an elevational view of the constant flush assembly;

FIG. 3 is an elevational view as in FIG. 2 with the tab pulled for flushing;

FIG. 4 is an elevational view of the plug;

FIG. 5 is an elevational view partly in section of an alternative embodiment of the invention; and FIG. 6 is an elevational view of still another embodiment.

The system with which the invention is employed has a catheter 10 which is insertable in a blood vessel of a patient, a main tube 11 and a transducer 12, the main tube connecting the catheter to the transducer. A fluid supply 13 is connected to the main tube through a constant flush valve assembly 15. The flush valve assembly is adapted to supply fluid such as a physiological solution at a very slow rate as, for example, three cc. plus or minus one cc. per hour to six cc. plus or minus one cc. per hour. The assembly has a fast flush bypass permitting an attendant to supply fluid at a much higher rate to the system.

Referring to FIG. 2, the constant flush assembly includes a tube 20 from the fluid supply 13 which is preferably under a pressure of 300 mm. of mercury. The tube 20 is connected to one leg 21 of a T fitting 22. The T fitting has another leg 23 which is connected to a curved, flexible tube 24 which is in turn connected to a capillary restrictor 25. The capillary restrictor 25 is connected to the main tube by another T fitting 26. Fluid under pressure from the supply 13 continuously flows into the main tube 11 and, hence, to the patient through the capillary restrictor 25.

A bypass flush valve is shown at 30. The valve includes a plug 31 (see also FIG. 4) having an upstream end 32 projecting into the third leg 33 of the T fitting 22. The plug also has a downstream end 35 projecting into a leg 36 of a T fitting 37 by which the flush valve is connected to the main tube 11. The plug has a central collar 40 having surfaces on each side which abut the legs 33 and 36 of the T fittings 22 and 37, respectively. The collar 40 may be provided with an annular rib 41 which assures a snug leak-tight engagement of the collar with the surrounding sleeve to be described.

The upstream and downstream ends of the plug 31 have longitudinal grooves 45 which merge into radial grooves 46 in the axially-facing surfaces of the collar 40 and form fluid passageways.

An elastomeric sleeve 50 surrounds the collar 40 and rib 41 and the legs 33 and 36 of the respective T fittings. The sleeve has a pull tab 51 which overlies the area where the grooves 45 are placed in the plug. When the sleeve is in its normal position as shown in FIG. 2, its snug fit around the collar 40 and rib 41 of the plug 31 blocks flow of fluid from the supply 13 around the plug to the main tube 11. A column of fluid in the upstream groove 45 and the radial groove 46 is blocked by its contact with the sleeve from passing around the collar to the downstream groove and main tube 11. Similarly, on the downstream side of the collar, the fluid in the main line 11 branches up to the leg 36 of the T fitting 37 and stands in the downstream groove 45 and the downstream radial groove 46 in the plug. That column of fluid bears against approximately 0.090" diameter area (created between radial groove 46 and leg 36 of T fitting 37) on the sleeve. This is such a small area of resilient material that it has no significant effect in absorbing pulsations from flow from the patient to the transducer.

When it is desired to flush the system, the sleeve 50 is deformed, as seen in FIG. 3, by pulling on the tab 51 to pull the sleeve away from the collar in the area adjacent to the upstream and downstream grooves. The opening up of that space permits fluid to flow rapidly around the collar 40 and into the main tube.

Sometimes a high velocity of flush fluid is desired as, for example, when setting the system up and filling up the lines to the transducer and catheter. At other times, it may be desired to have a much slower velocity as, for example, when the cathether is in the patient and the line to the catheter is to be flushed. The pull tab enables the attendant to vary the size of the passageway around the collar and thus to rather precisely regulate the velocity of the flow.

On other occasions, the attendant may wish to have a one-handed flushing operation. In such event, the resilient sleeve can simply be squeezed in order to bow or deform the sleeve in the area of the grooves so as to permit flushing fluid to flow.

One alternative embodiment of the invention is shown in FIG. 5. There, a single direct T connection 54 through a plug 55 surrounded by a resilient sleeve 50 is provided to connect the supply 13 to the main line 11. In this alternative embodiment, the capillary restrictor is embodied in the plug 55. The collar 56 on the plug has an external minute groove 57 which connects a pair of internal axial bores 58 and radial ports 59. The groove 57 is formed by a laser or by a tool, and when enclosed by the resilient sleeve, provides the capillary restrictor which permits metered continuous flow of fluid at rates of around three and six cc. per hour, as described above. It should be understood that surface grooves in the plug, as in the first embodiment, could be substituted for the axial bores 58 without departing from the invention.

In another alternative shown in FIG. 6, the plug has an axial restrictor orifice 60 connecting end bores 61.

The operation of the first and second alternative forms of the invention are substantially the same as the operation of the embodiment first described in that normally fluid is supplied to the main tube 11 at a very slow rate. However, when the sleeve is deformed as by pulling on the pull tab 51 or by squeezing the tube, a flushing fluid will enter the main tube 11.

Having described my invention, I claim:

1. In a constant flush system, including a catheter, a transducer, a main tube connected between said catheter and said transducer, and a fluid supply, a flow control connecting said fluid supply to said main tube, comprising, means forming a capillary flow path from said fluid supply to said main tube, a bypass flush valve from said fluid supply to said main tube comprising, a plug having a central annular collar, longitudinal grooves in said plug from each of its ends to said collar, a resilient sleeve normally surrounding said collar in fluid-tight relation, means connecting said sleeve between said supply and said main tube, the end portions of said plug being of a reduced diameter, fittings connected to said fluid supply and said main tube, said fittings receiving said reduced plug ends and abutting said collar, said grooves having radial passages between said collar and said fittings to provide passageways to the external surface of the said collar while permitting minimal exposure of said sleeve to a column of fluid.

2. A constant flush assembly as in claim 1 in which the outside diameter of said collar and said fittings are of substantially the same dimension, said collar and fittings being in abutting relation so as to eliminate annular grooves in said system which might entrap bubbles.

* * * * *